United States Patent [19]

Larsson et al.

[11] Patent Number: 4,532,232

[45] Date of Patent: Jul. 30, 1985

[54] LECTIN-CONTAINING SEPARATION AGENT

[75] Inventors: Per-Olof Larsson, Lund; Klaus Mosbach, Furulund, both of Sweden; Axel Borchert, Frankfurt am Main, Fed. Rep. of Germany

[73] Assignee: Pernovo AB, Perstorp, Sweden

[21] Appl. No.: 568,185

[22] PCT Filed: Apr. 19, 1983

[86] PCT No.: PCT/SE83/00147

§ 371 Date: Dec. 23, 1983

§ 102(e) Date: Dec. 23, 1983

[87] PCT Pub. No.: WO83/03776

PCT Pub. Date: Nov. 10, 1983

[51] Int. Cl.$^3$ .................. B01J 20/24; B01D 15/08; G01N 33/54

[52] U.S. Cl. .................. 502/403; 210/502; 210/656; 210/500.27; 435/176; 435/177; 435/276; 502/7

[58] Field of Search ............... 502/401–404, 502/7; 210/502, 656

[56] References Cited

U.S. PATENT DOCUMENTS 4,406,792  9/1983  Glad et al. .................. 210/656
4,446,275  5/1984  Filka et al. ................ 210/502.1

Primary Examiner—P. E. Konopka
Attorney, Agent, or Firm—Poms, Smith, Lande & Rose

[57] ABSTRACT

A separation agent composed of a water insoluble solid substance with a convatently bound lectin. Said solid substance is structurally composed of a water insoluble silica or silicate material as basic material and via a linkage to silicon atoms in the silica or silicate material, a covatently bound lectin.

5 Claims, No Drawings

LECTIN-CONTAINING SEPARATION AGENT

This invention relates to a separation agent consisting of a water insoluble solid substance containing a covalently bound lectin.

Lectins, especially Concanavalin A, have earlier been bound to solid substances such as agarose. The resulting material has been used for the separation of various carbohydrates, carbohydrate-related substances, organelles and even whole cells (Concanavalin A as Tool, H. Bittiger and H. P. Schnebli, John Wiley and Sons, New York, 1976).

The polymers which have been used as a basic material in these separation agents, for example agarose and polymethacrylic acid, have the drawback of leading to bad flow characteristics due to poor rigidity of the polymer and bad separation characteristics.

According to the present invention there has now been provided a separation agent of the above-mentioned type, which has superior flow and separation characteristics and which is well suited for use in connection with for example high performance liquid chromatography (HPLC). The separation agent according to the invention is characterized in that the solid substance structurally is composed of a water insoluble silica material or silicate material as a basic structure and via a linkage to silicon atoms in said silica or silicate material, a covalently bound lectin.

The expression "silica material" is herein intended to mean silicic acid in more or less dehydrated form, including silica. The basic material may be non-porous or porous silica or glass particles, which are known per se as carrier material in several applications, for example in biochemical determination methods, but can also consist of the inner wall of a tube or be a disk. The lectin is covalently bound to an alkylene chain which contains 1–22, preferably 2–18, carbon atoms and optionally being interrupted by one or more oxygen, sulphur or nitrogen atoms and/or being substituted with one or more hydroxyl groups. Except for the case of amide and ester groups, preferably at most 1 atom of a kind other than carbon and hydrogen is bound to one and the same carbon atom in the chain. The alkylene chain is in turn bound, optionally via an intermediate silicon atom, preferably to an oxygen atom belonging to a hydroxyl group, said hydroxyl group being bound to a silicon atom in the basic material for the present separation agent. The alkylene chain may also be optionally bound directly to a silicon atom in said basic material.

The introduction of the bridge-forming alkylene chain structure and the lectin in the silica or silicate material is preferably performed in two steps. A substituent which corresponds to the alkylene chain and which contains a reactive structure such as for example an epoxy or carboxyl group is introduced in the first step. In the second step the lectin is added which can react with the functional structure on the silica. In some cases a condensation-promoting agent such as a carbodiimide may also be added.

The invention will be illustrated by means of examples in the following text.

EXAMPLE 1

Preparation of Silica Comprising Epoxy Groups

To 20 g porous silica (LiChrosorb Si 1000, 10 $\mu$m, E Merck, Darmstadt, Federal Republic of Germany), dried at 200° C. over night and then suspended in 500 ml Na-dried toluene was added 200 microliter triethylamine (potassium hydroxide-dried) and 10 ml $\gamma$-glycidoxypropyltrimethoxysilane. The mixture was reflux boiled under nitrogen for 16 hr. in a flask fitted with a teflon stirrer. Thereafter the substituted silica was filtered off and washed on a glass filter funnel with toluene, acetone and diethyl ether and finally dried at reduced pressure. A sample of the obtained product was analyzed with respect to epoxy groups (reaction with 3 M sodium thiosulphate for 1 hr. at pH 7 and determination of librated hydroxyl ions by addition of acid (pH-stat; 0.10 M hydrochloric acid)). Materials based on LiChrosorb Si 1000 contained about 50 $\mu$mole epoxy groups/g.

EXAMPLE 2

Preparation of Silica Containing Diol Groups 3 g silica containing epoxy groups (see example 1) was suspended in 300 ml of 0.03 M hydrochloric acid. The mixture was kept at 50° C. with stirring for 2 hours. The obtained diol-containing material was filtered and washed with water, ethanol and ether and finally dried at reduced pressure.

EXAMPLE 3

Preparation of Silica Containing Aldehyde Groups 3 g silica containing diol groups (see example 2) were suspended in 50 ml 90% acetic acid and 5 g sodium periodate added in portions. The mixture was stirred carefully for 2 hours at room temperature. The aldehyde-containing silica was filtered, washed with water, acetone and ether and dried at reduced pressure.

EXAMPLE 4

Preparation of Silica Containing Tresyl Groups 3 g silica containing diol groups (see example 2) was dried in a vacuum at 50° C. for 4 hours and then suspended in 20 ml of sodium-dried acetone. 1 ml of pyridine was added followed by 0.5 ml tresyl chloride under vigorous stirring. The tresyl chloride was obtained from Fluka, Buchs, Switzerland. Tresyl chloride is also known as 2,2,2-trifluoroethanesulfonyl chloride. The tresyl group is the 2,2,2-trifluorethanesulfonyl group. After 30 min the tresyl group-containing silica was filtered off and washed on a glass filter with 200 ml of acetone, and finally dried under reduced pressure.

EXAMPLE 5

Preparation of Silica Containing Bound Lectin (Via Silica Containing Epoxy Groups)

1 g silica containing epoxy groups (see example 1) was suspended in 5 ml 0.1 sodium phosphate buffer pH 8.0, containing 50 mg Concanavalin A (obtained from Sigma, St. Louis, Mo., USA). The suspension was stirred carefully for 24 hours at 4° C. The lectin-containing silica was filtered off on a glass filter and washed with the above buffer. The Concanavalin A-silica was stored moist at 4° C.

Lectin-containing silica was suspended in 3 ml of saturated sucrose solution and the spectrum (240 nm–320 nm) recorded. The absorbance at 280 nm was used to calculate the concentration. The absorbance at 280 nm for a 1 percent by volume solution was equal to 10. A typical value is 2 mg Concanavalin A/g silica.

EXAMPLE 6

Preparation of Silica with Bound Lectin (Via Silica with Aldehyde Groups)

1 g silica with aldehyde groups (see example 3) was suspended in 5 ml 0.1 M sodiumphosphate buffer pH 7.5 containing 100 mg Concanavalin A. The suspension was stirred carefully for 16 hours at 4° C. 100 mg of sodium-borohydride was then added in portions under 30 min. After 4 hours the lectin-containing silica was isolated, washed, analyzed and stored as described in example 5. Typical lectin content is 60 mg Concanavalin A/g silica.

EXAMPLE 7

Preparation of Silica Containing Lectin (Via Silica Containing Tresyl Groups)

1 g silica containing tresyl groups (see example 4) was suspended in 5 ml 0.1 M sodium phosphate pH 7.5 containing 100 mg Concanavalin A. The suspension was stirred carefully for 16 hours at 4° C. Any remaining tresyl groups were subsequently eliminated by treatment with TrisHCl buffer (0.1 M, pH 7.5) for 1 hour. The lectin-containing silica was isolated, washed, analyzed and stored as described in example 5. Typical lectin content is 60 mg Concanavalin A/g silica.

EXAMPLE 8

Separations of Sugar with Lectin-Containing Silica

The separation was carried out with HPLAC-equipment (High Performance Liquid Affinity Chromatography). An Altex pump (model 110 from Altex Scientific Inc., Berkley, Calif., USA) was used together with a UV detector (SpectroMonitor III from Laboratory Data Control, Riviera Beach, Fla., USA).

Lectin-containing silica according to examples 5, 6 and 7 was packed in stainless steel columns (5×0.5 cm or 5×10 cm; total volume 1 and 2 ml respectively) using a packing technique described by P. A. Bristow et al., J. Chromatography, 131 (1977) 57. The lectin-containing silica was kept suspended in 50% sucrose during the packing procedure.

The chromatographic runs were carried out at room temperature. The pressure drop was 1-2 MPa at a flow rate of 1 ml/min.

A mixture of glycosides (1–10 μg) was injected in the flow, the retention times noted and the respective k'-values, "column capacity ratio" calculated:

$$k' = \frac{T_e - T_o}{T_o}.$$

$T_e$ is the retention time of the glycoside in question, $T_o$ is the "retention" time for an unretarded substannce. A high k'-value indicates a strong interaction between the lectin-containing silica and the glycoside.

The table shows representative results from a large number of separation experiments. In all experiments a mixture of p-nitrophenyl-α-D-glucoside, p-nitrophenyl-β-D-glucoside and p-nitrophenyl-α-D-mannoside was resolved. The table give k'-values for p-nitrophenyl-α-D-mannoside in combination with different types of Concanavalin A-silica. The table shows that the K'-value for the mannoside could be varied between 0.5 and 17. The k'-value for the α-D-glucoside could be varied up to 3 and the k'-value for the β-D-glucoside could be varied up to 0.7 (not shown in the table).

| Preparation number: | 1 | 2 | 3 | 4 | 5 | 6 |
| --- | --- | --- | --- | --- | --- | --- |
| Pore size (Å) | 100 | 100 | 1000 | 1000 | 1000 | 1000 |
| Coupling according to example number: | 5 | 6 | 6 | 6 | 6 | 7 |
| Concanavalin A content (mg/g) | 2 | 10 | 25 | 60 | 80 | 60 |
| k' | 0.5 | 2.1 | 3.8 | 16 | 12 | 17 |

EXAMPLE 9

Separation and Purification of the Glycoprotein Peroxidase by Chromatography on Lectin-Containing Silica Equipment and procedures as in example 8

A sample containing 4 mg of protein in 4 ml of 0.1 M phosphate buffer pH 7 was injected on a column containing Concanavalin A-silica (60 mg/g; prepared as in example 6). The peroxidase was absorbed on the column whereas remaining protein passed the column unretarded. A pulse of α-D-methyl-glucoside (4 ml; 25 millimolar) eluted a pure peroxidase as judged from spectrophotometric data. A gradient, 0–20 mM, of the same methylglucoside could also be used to elute the peroxidase. The purification lasted in the first case 15 minutes and in the second case 30 minutes.

EXAMPLE 10

Peroxidase-binding Capacity of Concanavalin A-silica

Equipment and procedures essentially as in example 8

Through a column filled with 1 g of Concanavalin A-silica (60 mg/g; prepared as in example 6) was pumped a peroxidase containing solution until the column became saturated. The binding capacity was then calculated as 12 mg peroxidase/g of silica.

EXAMPLE 11

Separation and Purification of the Glycoprotein Glucose Oxidase by Chromatography on Lectin-Containing Silica Equipment and procedures as in example 8

A sample containing 4 mg of protein in 4 ml 0.1 M sodium phosphate buffer, pH 7.0, was injected on a column filled with Concanavalin A-silica (60 mg/g; prepared as in example 6). The glucose oxidase was strongly absorbed to the lectin-containing silica and could not be eluted with methyl glucoside. A pulse of 0.2 M glycine-HCl buffer, pH 2.8, was required for elution. The drastic condition for elution did not harm the packing material or the enzyme.

EXAMPLE 12

Stability of Lectin-Containing Silica

One column was used 60 times without any noticeable change of the K'-value for chromatographed substances.

We claim:

1. A separation agent comprising a water insoluble solid selected from the group consisting of silica material and silicate material, said solid having lectin bound thereto, said lectin being bound to said solid via an alkylene chain, said alkylene chain having from 1 to 22 carbon atoms.

2. A separation agent according to claim 1 wherein said solid is silica.

3. A separation agent according to claim 2 wherein said silica is porous.

4. A separation agent according to claim 1 wherein said alkylene chain is interrupted by at least one atom selected from the group consisting of oxygen, sulfur and nitrogen.

5. A separation agent according to claim 4 wherein said alkylene chain is bound to said solid via an intermediate second silicon atom.

* * * * *